United States Patent
Cooker

(10) Patent No.: US 6,656,501 B1
(45) Date of Patent: Dec. 2, 2003

(54) ORAL DELIVERY SYSTEM AND METHOD FOR MAKING SAME

(76) Inventor: John T. Cooker, 5023 Smith Rd., Rohrersville, MD (US) 21779

( * ) Notice: Subject to any disclaimer, the term of this patent is extended or adjusted under 35 U.S.C. 154(b) by 0 days.

(21) Appl. No.: 09/614,243

(22) Filed: Jul. 12, 2000

Related U.S. Application Data

(60) Provisional application No. 60/151,901, filed on Sep. 1, 1999.

(51) Int. Cl.$^7$ ................................................. A61K 9/48
(52) U.S. Cl. ...................... 424/452; 424/451; 424/453; 424/400; 424/465
(58) Field of Search ................................. 424/465, 453, 424/440, 480, 489, 438, 473, 451, 452

(56) References Cited

U.S. PATENT DOCUMENTS

| | | | |
|---|---|---|---|
| 4,177,254 A | | 12/1979 | Khan et al. .................... 424/16 |
| 4,238,510 A | | 12/1980 | Cherukuri et al. .............. 426/5 |
| 4,803,076 A | * | 2/1989 | Ranade ......................... 424/438 |
| 4,820,524 A | | 4/1989 | Berta ........................... 424/474 |
| 4,894,233 A | * | 1/1990 | Sharma et al. ............... 424/440 |
| 4,959,219 A | * | 9/1990 | Chow et al. .................. 424/480 |
| 4,966,771 A | | 10/1990 | Berta ........................... 424/478 |
| 5,089,270 A | * | 2/1992 | Hampton et al. ............ 424/465 |
| 5,098,425 A | * | 3/1992 | Eckenhoff .................... 424/438 |
| 5,114,720 A | | 5/1992 | Littell et al. ................. 424/478 |
| 5,198,229 A | * | 3/1993 | Wong et al. .................. 424/473 |
| 5,296,233 A | | 3/1994 | Batista et al. ................ 424/463 |
| 5,314,537 A | | 5/1994 | Berta ........................... 118/30 |
| 5,527,542 A | | 6/1996 | Serpelloni et al. ........... 424/488 |
| 5,567,439 A | | 10/1996 | Myers et al. ................. 424/486 |
| 5,571,547 A | | 11/1996 | Serpelloni et al. .......... 426/103 |
| 5,725,884 A | | 3/1998 | Sherwood et al. .......... 424/489 |

OTHER PUBLICATIONS

"ABCs of the Human Body", 1987, Editor, Alma E. Guinnes, p. 240.
"The Human Body", Vol.: Digestion, 1984, Editor, Beryl Leith, pp. 60–61.

* cited by examiner

Primary Examiner—Thurman K. Page
Assistant Examiner—Robert M. Joynes
(74) Attorney, Agent, or Firm—Raymond Nuzzo

(57) ABSTRACT

The present invention is directed to improved oral dosage forms that are significantly easier to swallow. In accordance with the present invention, the oral dosage forms are configured to have relatively greater weight and/or density to effect partial or total submergence in the liquid with which the oral dosage form is taken. In one embodiment, a filler is added to the ingredients of the oral dosage form. In another embodiment, a filler is added to the medium of the oral dosage form. In a further embodiment, a filler is added to the exterior of the oral dosage form. In another embodiment, a relatively heavier, denser or larger amount of ingredient is used to formulate the oral dosage form. In yet a further embodiment, a binder is used to increase the weight and/or density of the oral dosage form. In yet another embodiment, a combination comprising a binder and a relatively heavier, denser or larger amount of ingredient is used to formulate the oral dosage form. In accordance with the present invention, oral dosage forms are configured to have a predetermined weight and/or density while conforming its size to what can be comfortably swallowed.

6 Claims, 3 Drawing Sheets

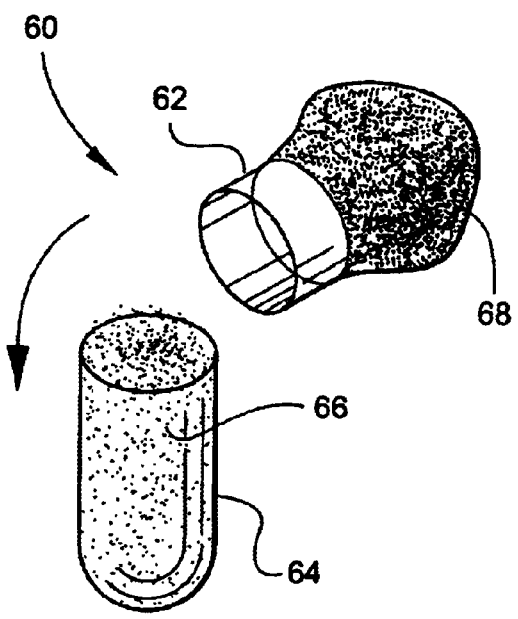
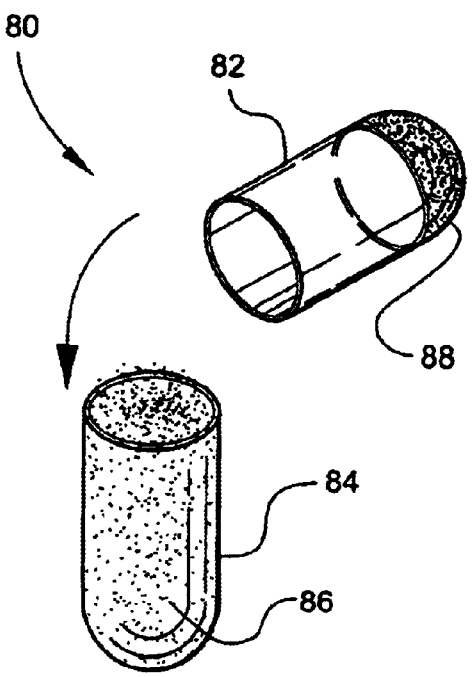
Fig. 5            Fig. 6
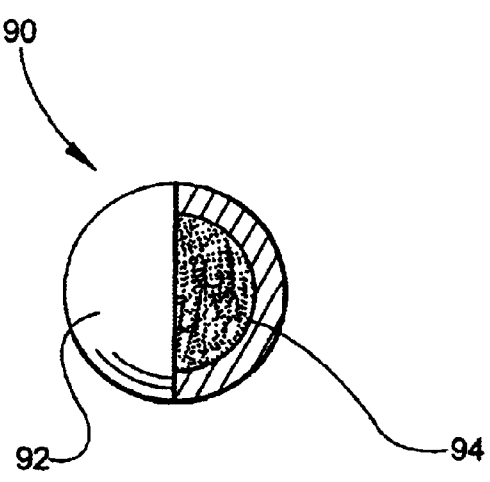
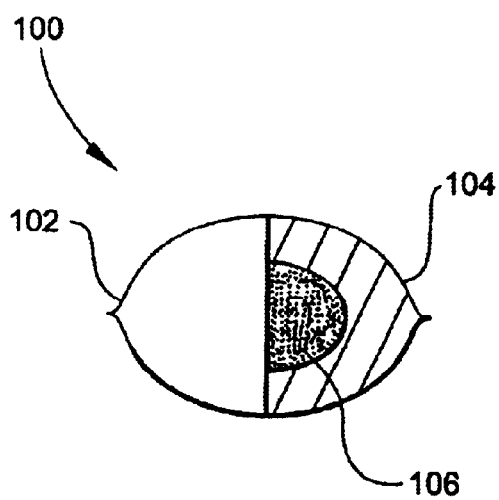
Fig. 7            Fig. 8

ORAL DELIVERY SYSTEM AND METHOD FOR MAKING SAME

This application claims the benefit of commonly owned U.S. Provisional Application Ser. No. 60/151,901, filed Sep. 1, 1999.

BACKGROUND OF THE INVENTION

COPYRIGHT NOTICE

© Copyright 2000, John T. Cooker. All rights reserved.

A portion of the disclosure of this patent document contains material that is subject to copyright protection. The copyright owner has no objection to the facsimile reproduction by anyone of the patent document or the patent disclosure, as it appears in the USPTO patent file or records, but otherwise reserves all copyright rights whatsoever.

1. Field of the Invention

The present invention generally relates to an oral delivery system.

2. Problem to be Solved

Over the years, the pharmaceutical industry has developed a variety of medications, medicaments, vitamins, nutritional supplements, etc. (collectively referred to herein as "oral dosages") that can be taken orally and which are in the form of capsules, tablets, gel caps and their like (collectively referred to herein as "oral dosage forms"). However, many consumers have experienced difficulty in swallowing such oral dosage forms. Specifically, many types of available oral dosage forms become buoyant on the liquid with which they are taken. This is especially the case with capsules which are hardened reservoirs of gelatin filled with powdered ingredients and air. As a result of such a configuration, the powdered ingredients and air become bubbles sealed in gelatin.

The buoyancy of the oral dosage forms on the liquid causes discomfort and creates difficulty in swallowing. Specifically, the buoyancy property creates the following problems:

1) the buoyancy of the oral dosage form works against the downward motion of swallowing and also reduces control of the oral dosage form by the tongue and pharynx muscles;

2) the dry gelatin outer surface of a capsule or gel cap, when wetted, quickly becomes sticky and easily adheres to surfaces it contacts. As a result, the oral dosage form may be left behind as it follows the liquid down the pharynx and esophagus thereby requiring successive swallows of additional liquid to flush down the oral dosage form; and 3) a capsule, while floating on the liquid, may move out of its intended aligned position in which the narrow end of its cylindrical shape points toward the pharynx and esophagus and as a result, is swallowed at an uncomfortable angle, possibly becoming lodged in the process.

Oral dosage forms that have a cylindrical, oval or rectangular shape (but not round), and are not heavy enough to sink on the liquid with which they are taken may move out of their aligned position while being propelled by the tongue toward the pharynx and esophagus thereby being swallowed at an uncomfortable angle.

The pharmaceutical industry has attempted to solve these problems by developing various oral dosage forms that supposedly have improved swallowabilty. In their attempt to solve the aforementioned problem relating to swallowability, the pharmaceutical industry has focused on the size, shape and surface composition of the capsules, tablets, gel caps, etc. In another attempt to address the problem of swallowability, the industry developed and produced cylindrical-shaped tablets which were to replace round shaped tablets, (i.e. a capsule shaped tablet),. One result of the pharmaceutical industry's attention to this problem was the development of the gelatin-coated caplet which not only addressed the problems relating to swallowability but also consumers' wariness of capsule tampering. Such a caplet is disclosed in U.S. Pat. No. 5,314,537. Although the gelatin-coated caplet has provided improvement in the swallowability of such caplets, the pharmaceutical industry's attempts to solve this problem are basically limited to the application of coatings to the exterior of the caplet, tablet, etc.

Despite the improvements discussed above, consumers still continue to express desire for oral dosage forms that exhibit improved swallowability characteristics.

It is therefore an object of the present invention to provide new and improved oral dosage forms that solve the problems discussed above.

Still other objects and advantages of the present invention will in part be obvious and will in part be apparent from the specification.

SUMMARY OF THE INVENTION

The present invention is directed to improved oral dosage forms that are significantly easier to swallow. In accordance with the present invention, the oral dosage forms are configured to have relatively greater weight and/or density to effect partial or total submergence in the liquid with which the oral dosage form is taken.

In one embodiment, the present invention is directed to an oral dosage form for ingestion with liquid, comprising, an active ingredient with or without excipient ingredients, and a substance having a predetermined weight that effects at least partial sinking of the oral dosage form in the liquid.

In one embodiment, the substance is a filler that is added to the active ingredient and, if used, the excipient, of the oral dosage form.

In another embodiment, a filler is added to the medium of the oral dosage form.

In a further embodiment, a filler is added to the exterior of the oral dosage form.

In another embodiment, a relatively heavier, denser or larger amount of active and excipient ingredients are used to formulate the oral dosage form.

In yet a further embodiment, the substance is a binder that is used to increase the weight and/or density of the oral dosage form.

In yet another embodiment, a combination comprising a binder and a relatively heavier, denser or larger amount of ingredient is used to formulate the oral dosage form.

In accordance with the present invention, oral dosages are configured to have a predetermined weight and/or density while conforming its size to what can be comfortably swallowed.

Oral dosage forms have a variety of physical characteristics, such as the medium used for transport. Thus, the present invention teaches a variety of configurations of oral dosage forms and methods for making these oral dosage forms, that solve the aforementioned problems and deficiencies associated with conventional oral dosage forms.

The configurations and methods of the present invention are applicable to the three major types of oral dosage forms: (1) capsules, (2) tablets and caplets, and (3) soft-gels.

BRIEF DESCRIPTION OF THE DRAWINGS

The features of the invention are believed to be novel. The figures are for illustration purposes only and are not drawn to scale. The invention itself, however, both as to organization and method of operation, may best be understood by reference to the detailed description which follows taken in conjunction with the accompanying drawings in which:

FIG. 5 is a side elevational view of yet another embodiment of a capsule configured in accordance with the present invention wherein a filler substance is attached or adhered to the exterior of the capsule.

FIG. 6 is a side elevational view of yet a further embodiment of a capsule configured in accordance with the present invention wherein the filler is molded into one of the capsule portions.

FIG. 7 is top plan view of one embodiment of a tablet configured in accordance with the present invention wherein a tablet is embedded in one portion of the filler.

FIG. 8 is a top plan view of one embodiment of a softgel configured in accordance with the present invention wherein a filler is embedded in one portion of the softgel.

DETAILED DESCRIPTION OF THE INVENTION

Figure 1:
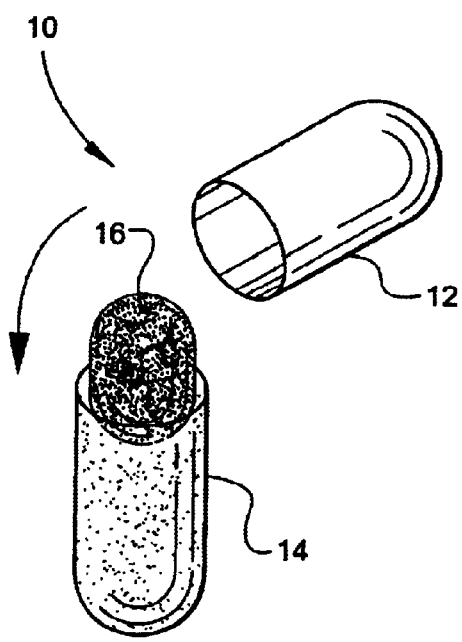
FIG. 1 is a side elevational view of one embodiment of a capsule configured in accordance with the present invention wherein a filler is added to the capsule.
Figure 2:
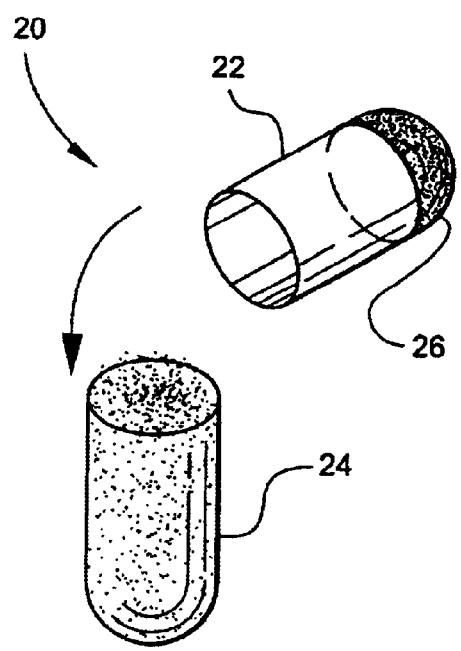
FIG. 2 is a side elevational view of a capsule having thereon indicia to indicate the portion of the capsule having concentrated weight.

In describing the preferred embodiments of the present invention, reference will be made herein to FIGS. 1–10 of the drawings in which like numerals refer to like features of the invention.

It has been found that by increasing the weight of oral dosage forms, unexpected superior results are achieved in that the swallowability of the oral dosage forms is significantly improved. In particular, it has been found that an oral dosage form configured to have a relatively greater weight than that of a conventional, but same type, oral dosage form, has significantly improved swallowability characteristics. Specifically, the "weighted" oral dosage form results in a significantly greater gravitational force being exerted upon the oral dosage form which facilitates direct and relatively quicker passage of the oral dosage form through the pharynx and into the stomach.

It has also been found that increasing the density of oral dosage forms, unexpected superior results are achieved in that the swallowability of the oral dosage forms is significantly improved. In particular, it has been found that an oral dosage form configured to have a relatively greater density than that of a conventional, but same type, oral dosage form has significantly improved swallowability characteristics. Specifically, the oral dosage form having the greater density has significantly less buoyancy with respect to the liquid which is taken with the oral dosage form. (As described in the foregoing discussion, it is buoyancy that resists the swallowing process). Thus, by significantly reducing buoyancy of the oral dosage form, the swallowability of the oral dosage form is greatly enhanced.

It also has been found that increased weight and/or density concentrated at a particular end or side of an oral dosage form maintains the oral dosage form in a preferred and intended alignment by vertically positioning oral dosage form as it is swallowed. The heavier end is positioned such that it points generally in the direction of the pharynx and the lighter end points generally toward the mouth. As a result, swallowability is significantly enhanced because the probability of the oral dosage form being swallowed at an uncomfortable angle is significantly reduced.

In a preferred embodiment, the increased weight and/or density concentrated at a particular end or side of an oral dosage form is such as to cause the oral dosage form to sink entirely in the liquid which is taken with the oral dosage form while maintaining the vertical alignment of the oral dosage form as discussed above. In an alternate embodiment, the increased weight and/or density concentrated at a particular end or side of an oral dosage form is such as to cause the oral dosage form to partially sink in the liquid while maintaining the vertical alignment of the oral dosage form as discussed above.

As described above, in one embodiment of the present invention, a filler is added to the ingredients of the oral dosage form. The filler may be in solid, semi-solid, liquid or powder form. Furthermore, the filler may be inactive or may provide an active function, e.g. digestive aid. The filler can be formulated out of any commercially available soluble or insoluble filler including sucrose, dextrose, lactose, fructose, microcrystaline cellulose, calcium carbonate, sorbitol, xylitol, isomalt, gelatin, and starches. However, it is to be understood that other types of commercially available fillers can be used as well. The filler can be added at any convenient time during the filling process. In one embodiment, the filler material is comprised of solid sucrose granules which are added to the ingredients of an oral dosage form. In another embodiment, a solid sucrose portion is molded or adhered to the inside of an oral dosage form. In a further embodiment, the filler is applied as a relatively thick shell of sorbitol to the oral dosage form.

In accordance with the present invention, the filler is at one end of the oral dosage form. In another embodiment, the filler is concentrated at the opposite end of the oral dosage form. In such configurations, the end of the oral dosage form having the filler is relatively heavier than the other end thereby causing the weighted end to sink first in the liquid taken with the oral dosage form. The oral dosage form becomes vertically positioned due to the weighted end sinking first. In a preferred embodiment, the oral dosage form having a weighted end includes indicia to indicate which end of the oral dosage form is weighted. In the case of capsules, the indicia enables consumers to align the heavier end first in their mouth so as to use the capsule's cylindrical shape to facilitate correct alignment of the capsule and movement of the capsule through the throat and into the esophagus. The indicia on the weighted end decreases the chance of the oral dosage form becoming swallowed at an angle that causes discomfort. As a result, confidence is instilled in the consumer when using the oral dosage form. In one embodiment, the indicia on the weighted end of the oral dosage form is a predetermined color.

In another embodiment, the oral dosage form may be configured such that the filler is part of the medium, e.g. capsule, or formed to the medium. In such a configuration, a coating comprising the filler is disposed on the exterior surface of the medium of the oral dosage form. In a preferred embodiment, the thickness of the filler coating is between about 20 and 200 mils, inclusive. The filler coating may be irregular in shape. The filler coating may be adhered to the medium of the oral dosage form in many ways, e.g. coating, dipping, etc.

In a further embodiment, a relatively heavier or denser diluent is used as an ingredient of the oral dosage form. In particular, a portion of a powdered diluent used to bulk the volume of a capsule containing a small dosage of ingredients is replaced with solid granules in order to increase the weight and/or density. In one example, rice flour in solid granule form is used. Rice flour in solid granule form has a relatively greater density or weight and as a result, can be used in the same available oral dosage form volume thereby effecting a relatively heavier and denser oral dosage form.

In another embodiment, a binder is used to effect a relatively denser oral dosage form. Conventional capsules are typically filled with free flowing ingredients in powder form. However, conventional capsules do not use binders to adhere the free flowing ingredients. In accordance with the present invention, a binder is mixed with a portion of a capsule's ingredients in order to effect a significant increase in the density of the end product. In one embodiment, a starch binder is mixed with a portion of ingredients to form solids or semi-solids which, when dried and combined with the remaining ingredients, form a relatively denser end product. As a result, a smaller capsule can be used, or a relatively larger amount of ingredients can be used in the original capsule. This process of binding a portion of the ingredients of a capsule requires relatively less effort than producing a complete tablet of all the ingredients and the end product still retains the characteristics of a capsule, e.g. the capsules shiny, smooth surface.

In another embodiment, relatively large amounts of diluent and binder are combined to form a composition that is used to formulate a tablet in order to increase the weight and/or density of the tablet. In another embodiment, a binder and a portion of an active ingredient or diluent of a capsule are mixed to form a solid which when dried, is added to the other portions of capsule ingredients thereby eliminating the need for a filler.

It is to be understood that any of the aforementioned methods and techniques of the present invention may be used in any combination to increase the weight and/or density of an oral dosage form.

The ensuing description uses particular abbreviations for units of measure. To facilitate understanding of the ensuing description, the following key of abbreviations is provided:

| Unit of Measure | Abbreviation |
|---|---|
| liters | l |
| milliliters | ml |
| grams | g |
| milligrams | mg |
| Density | D |

It is to be understood that for purposes of facilitating understanding of the present invention, the ensuing description is in terms of the liquid with which the oral dosage form is taken as being water. However, it is to be understood that other liquids may be used, e.g. soda, juice, coffee, etc. and that the weight and/or density of the oral dosage form may have to be increased in accordance with the present invention to eliminate buoyancy of the oral dosage form on those types of liquids.

The ensuing description describes excipients which are used in the production of oral dosages. Excipients are generally described in U.S. Pat. No. 5,725,884.

In order to facilitate understanding of the present invention, the ensuing description is divided into separate discussions of each of the three types of oral dosage forms: (1) capsules, (2) tablets and caplets, and (3) soft-gels.

1) Capsules

As discussed above, conventional capsules, in effect are sealed powder and air. As mentioned in the foregoing discussion, the sealed powder and air have buoyant characteristics. In accordance with the present invention, a capsule is provided that is configured to sink in the liquid that is taken with the capsule. It has been found that sinking of the capsule in the liquid effects a significant improvement in the swallowability of the capsule without compromising other characteristics consumers find favorable, i.e. shiny, smooth surface. In accordance with the present invention, capsules are configured to have a relatively greater weight and/or density than water (the density of water is 1 g/ml @4° C.) without increasing the size of the capsule beyond consumer preference.

EXAMPLE 1

A typical conventional capsule of 50 mg of the popular nutritional supplement zinc contains excipients that weigh 462 mg. Its total weight is 512 mg in a size 0 capsule with a volume of 0.68 ml and has a density of: D=0.512 g/0.68 ml or 0.75 g/ml. Since the density of this capsule is less than 1 g/ml, it will float on water. In accordance with the present invention, the density D of the capsule is increased to about 0.29 g/ml by the addition of a solid sucrose filler weighing 250 mg at 0.1 ml. As a result, the end product (i.e. the modified capsule) will weigh 762 mg at a volume of 0.73 ml. Due to compression in the filling process, the capsule will only expand 0.05 ml. Thus, the density-augmented capsule will now have a density D that is equal to 0.762 g/0.73 ml, or 1.04 g/ml. The density-augmented capsule will sink in the water with which it is swallowed thereby overcoming the problems associated with capsule buoyancy discussed above. Specifically, the density-augmented capsule will significantly reduce the probability of the capsule moving out of correct alignment and being swallowed at an angle. It is to be understood that the density of the density-augmented capsule can be further augmented. However, in a preferred embodiment, the density augmentation is such that it does not increase the size of the capsule beyond what can be comfortably swallowed by consumers. However, it is to be understood that in the case of a veterinary application, particular animals may be able to swallow capsules having a size greater than the size preferred by consumers.

In Example 1 above, 250 mg or 32% of the total weight of the end product is the result of the addition of the solid sucrose filler. Since the range of capsule weight and density varies, the amount of the filler needed to achieve the objects of the present invention also will vary. In a preferred embodiment, the percentage of the total weight of the end product that is due to the addition of the filler ranges between 15% and 80%, inclusive. More preferably, the percentage of the total weight of the end product that is due to the addition of the filler ranges between 25% and 50%, inclusive, if the filler is used exclusively.

EXAMPLE 2

In this example, the 512 mg weight of the above conventional capsule is significantly increased at the same volume by the exchange of its powdered diluent for solid granules. Specifically, the 200 mg of a rice flour power diluent is replaced by 400 mg of sucrose solid granules. The sucrose solid granules require the same amount of space but weigh twice as much as the rice flour diluent. Thus, the weight of the capsule is increased to 712 mg at the same volume with a density $D = 0.712$ g/0.68 ml or 1.04 g/ml. Thus, the weight-augmented capsule will sink in water.

EXAMPLE 3

In this particular example, a binder is used to produce a capsule having a relatively greater density. For this particular example, the conventional zinc capsule as described above in Example 1, contains about 112 mg of powder zinc and other excipients and about 400 mg of the rice flour diluent. In this example, increasing the density of the capsule in accordance with the present invention comprises the following steps: (a) subtracting 200 mg of the rice flour diluent, (b) providing 200 mg of dry sorbitol, (c) mixing the sorbitol with liquid to form a syrup-like binder, (d) mixing the syrup-like binder with the remaining 200 mg of rice flour, (e) drying the mixture of the syrup-like binder and the rice flour, (f) forming granules from the dried mixture, and (g) adding the granules to the 112 mg of powder zinc and remaining excipients. As a result, the total capsule weight remains about the same but the volume of the capsule ingredients (zinc, excipients and binder) shrinks or decreases 0.2 ml allowing the use of smaller capsule portions. The density D of the end product would be 0.512 g/0.5 ml or 1.024 g/ml. This density is more than sufficient to allow the capsule to sink in water.

If water is to be used as the liquid medium with which the capsule is taken, then it is preferable that the density of the capsule be increased to at a density that is greater than 1 g/ml so as to effect sinking of the capsule in the water. However, it is to be understood that the density of the capsule, or any of the oral dosage forms, can be increased in accordance with the present invention to effect sinking of the oral dosage form in other types of liquids, e.g. soda, juices, coffee, milk, etc.

In order to produce the oral dosage forms in accordance with the present invention, particular, pertinent and novel manufacturing steps are implemented. These steps are described in the ensuing description.

Capsules typically are comprised of two portions or components that are pushed together to enclose the capsule ingredients. The capsule portions are pushed together by applying a predetermined force. This type of "enclosing" technique does not employ any type of steps to seal the capsule portions together after the predetermined force is applied. However, it has been found that the force currently being used in conventional processes to compress the ingredients to an effective density is not sufficient because the capsule ingredients tend to bounce back when the capsule portions are not sealed together. The method of the present invention includes a particular step that pertains to the application of such force. Specifically, the method of the present invention includes the step of applying a relatively greater force to the capsule portions, in comparison to the force applied in conventional capsule fabrication processes, in order to effect the extraction of air from the powdered ingredients. The extraction of air from the interior of the capsule facilitates swallowability of the capsule. Furthermore, the increased force facilitates the positioning of the filler and the ingredients within the capsule volume.

In another embodiment of the method of the present invention, the capsule portion holding the ingredients is configured to have a deeper well to accommodate the filler material. This is illustrated in FIG. 1. Capsule 10 generally comprises portions 12 and Portion 14 holds the ingredients during the filling process. In one embodiment, portion 14 is configured to have a relatively deeper "well" in order to accommodate filler material that is used to increase the weight and/or density of the capsule in accordance with the present invention. In such an embodiment, the length of portion 12 is increased to accommodate filler material or binders (see FIG. 2). In another embodiment, the length of portion 14 is increased to accommodate filler material or binders. In yet a further embodiment, the diameter of portions 12 and 14 are increased to accommodate larger amounts of filler materials or binders.

The filler may be configured to have any suitable shape. However, it has been found that if a single solid filler is used in a capsule, then the preferred shape of the filler should be generally spherical or oval in order to facilitate compacting powder ingredients and filling air gaps. In one embodiment, the filler is covered with a film material that prevents it from interacting with the ingredients.

In a further embodiment of the method of the present invention, the capsule components, e.g. portions 12 and 14, are formulated to have a relatively greater thickness to provide relatively greater strength to withstand the greater force resulting from addition of the filler. Furthermore, it is to be understood that the added thickness of the capsule portions also contributes to the increase in weight and density of the capsule in accordance with the present invention.

In another embodiment of the method of the present invention, a sealing process is used to hold the joined capsule portions in place. Specifically, this sealing process includes the step of applying an adhering agent around the seam of the filled and joined capsule portions.

In a further embodiment, a locking process is used to hold the joined capsule portions in place. In such a process, indentations or moldings are formed on the capsule cap and body. The indentations or moldings are used to lock the cap and body together. A plurality of indentations or moldings can be used to provide capsules varying lengths.

In yet another embodiment of the method of the present invention, when the weight of the capsule is increased to improve swallowability, as described above, the weight is concentrated at one end of the capsule. When such a configuration is used, indicia is applied to the weighted portion of the capsule. Such a configuration is shown in FIG.

2. Capsule 20 comprises portions 22 and 24. Portion 22 has indicia 26 to indicate that portion 22 is the weighted portion and that capsule 20 should placed in the consumer's mouth so that weighted portion 22 is pointing toward the opening of the esophagus. In one embodiment, the indicia comprises a color. However, it is to be understood that other types of indicia can be used, e.g. letters, numbers, etc.

Figure 3:
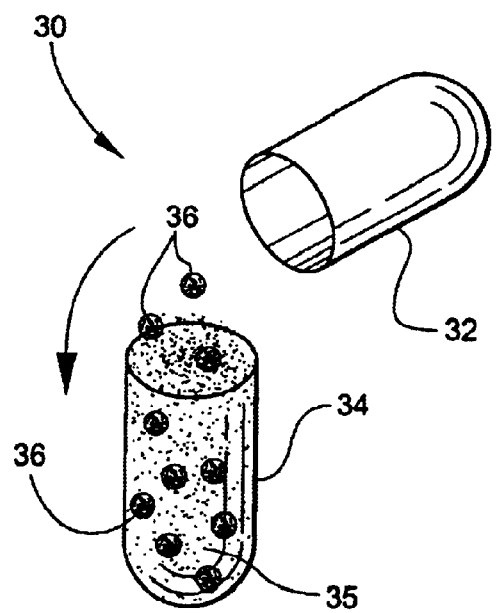
FIG. 3 is a side elevational view of a further embodiment of a capsule configured in accordance with the present invention wherein filler granules are added to the capsule.

Referring to FIG. 3, as described in the foregoing description, granules of a particular substance, e.g. sucrose solid granules, are added to the capsule to increase the weight and/or density of the capsule. Thus, the method of the present invention includes the steps of (a) providing capsule 30 that comprises capsule portions 32 and 34, (b) retaining portion 34 so that it is stationary, (c) depositing ingredients 35 to portion 34, (d) depositing granules 36 into portion 34, and (e) joining capsule portions 32 and 34 together. The method may also include the step of applying indicia to the weighted portion of capsule 30 in a manner as described above.

Figure 4:
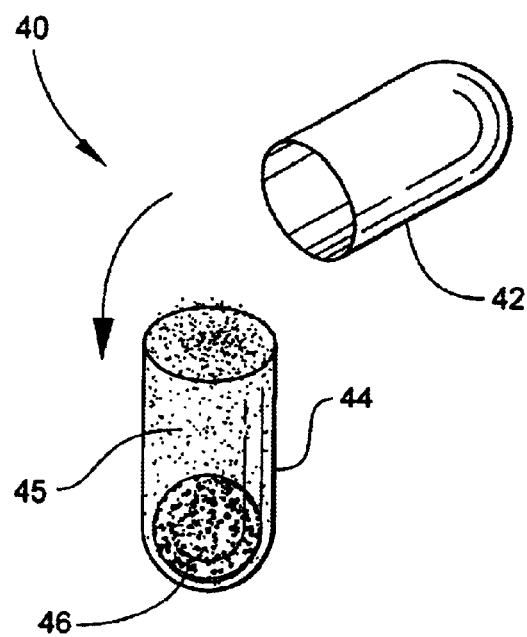
FIG. 4 is a side elevational view of yet a further embodiment of a capsule configured in accordance with the present invention wherein a single filler substance is added to the capsule.

Referring to FIG. 4, the method of the present invention also provides particular steps for using a single filler substance. Specifically, the method of the present invention includes the steps of (a) providing capsule 40 that comprises capsule portions 42 and 44, (b) retaining portion 44 so that it is stationary, (c) depositing ingredients 45 to portion 44, (d) depositing single filler substance 46 into portion 44, and (e) joining capsule portions 42 and 44. The method may also include the step of applying indicia to the weighted portion of capsule 40 in a manner as described above.

Referring to FIG. 5, the method of the present invention also provides particular steps for adding or attaching a filler substance to the exterior of either capsule portion. Specifically, the method of the present invention includes the steps of (a) providing capsule 60 that comprises capsule portions 62 and 64, (b) retaining portion 64 so that it is stationary, (c) depositing ingredients 66 into portion 64, (d) adhering or attaching filler substance 68 to the exterior surface of portion 62, and (e) joining capsule portions 62 and 64 together.

Referring to FIG. 6, the method of the present invention also provides particular steps for molding a filler substance into either of the capsule portions. Specifically, the method of the present invention includes the steps of (a) providing capsule 80 that comprises capsule portions 82 and 84, (b) retaining portion 84 so that it is stationary, (c) depositing ingredients 86 into portion 84, (d) molding filler substance 88 into portion 82, and (e) joining capsule portions 82 and 84 together. In an alternate embodiment of this method, the filler substance 88 is adhered to the inside of either of the capsule portions The method of the present invention also provides particular steps for adding a filler substance to the capsule by forming one or both of the capsule portions with the filler substance integral with the medium from which the capsule portions are made.

The solid filler described above can be standardized in order to facilitate automated manufacturing processes. The solid filler can be adhered to the inside of the cap portion of the capsule while the cap portion is still empty. Capsules typically are manufactured in standard sizes so that they may be handled by automatic filling machines. Such standard sizes and respective volumes are shown in Table I:

TABLE I

| Size | 00 | 0 | 1 | 3 | 3 | 4 |
|---|---|---|---|---|---|---|
| Volume (ml) | 0.95 | 0.68 | 0.50 | 0.37 | 0.30 | 0.21 |

In a preferred embodiment, the optimum size filler possible is adhered to the cap portion of the capsule. As an example and for purposes of illustration, Table II shows the filler weight needed to raise the powder ingredient density from 0.7 g/ml to 1.0 g/ml for a given capsule size:

TABLE II

| Size | 00 | 0 | 1 | 2 | 3 | 4 |
|---|---|---|---|---|---|---|
| Weight of 0.7 g/ml Powder Density (mg) | 665 | 476 | 350 | 259 | 210 | 147 |
| Filler Weight (mg) | 285 | 204 | 150 | 111 | 90 | 63 |

2) Tablets and Caplets

In accordance with the present invention, tablets and caplets are produced with relatively greater weight and density to improve swallowability of the tablets and/or caplets. The increase in weight and density is accomplished by adding a filler as described above. In one embodiment, the filler is added to the ingredients. For example, in one embodiment, a solid sucrose filler is molded in with the ingredients. In another example, the filler is embedded within the tablet ingredients.

In another embodiment, the filler is attached to the exterior of the tablet or caplet. This example is illustrated in FIG. 7. Tablet 90 comprises portions 92 and 94. Portion 92 is comprised only of filler. Portion 94 is embedded within the filler.

In yet another embodiment, the tablet is configured such that one side, end or portion of the tablet has concentrated weight and has indicia to indicate which side, end or portion has the concentrated weight.

In a further embodiment, increasing the weight and density of the tablet or caplet is accomplished by increasing a component of the tablet or caplet. In one embodiment, this is accomplished by increasing the weight of an excipient such as the binder ingredient.

In a preferred embodiment, the percentage of the total weight of the end product due to the addition of the filler or increase in the weight of the component is between about 15% and 90%, inclusive. More preferably, the percentage of the total weight of the end product due to the addition of the filler or increase in the weight of the component is between about 25% and 75%, inclusive. For example, 50% of the weight of a 400 mg tablet augmented with 200 mg of filler is the result of adding the filler. In this example, the original weight of the tablet has been doubled or increased about 100%.

The increase in weight and/or density provides significantly improved swallowability of particularly light, small sized tablets and caplets (i.e. under 300 mg, 4/10 ml).

Figure 9:
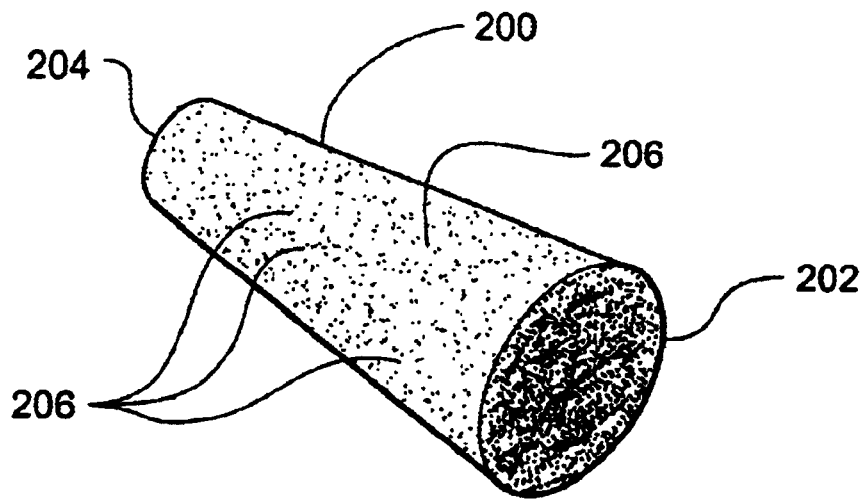
FIG. 9 is a perspective view of a conical-shaped tablet configured in accordance with the present invention wherein a filler is dispersed throughout the tablet.
Figure 10:
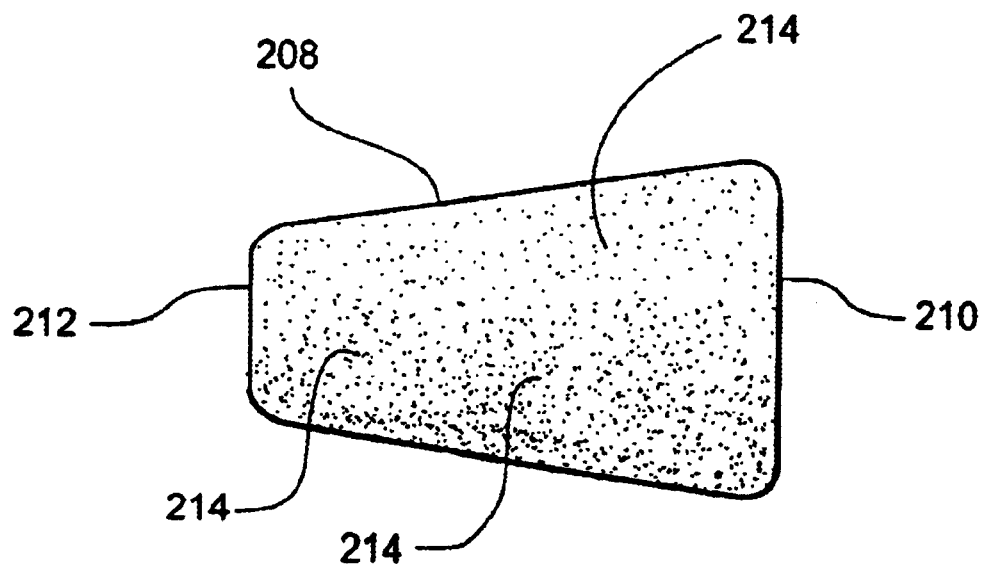
FIG. 10 is a top plan view of a generally trapezoidal-shaped tablet having filler dispersed throughout the tablet.

Referring to FIGS. 9 and 10, there are shown alternate embodiments of the tablets and caplets of the present invention. These embodiments utilize a particular shape having a swelled end which is substantially larger than the opposite end. For example, FIG. 9 shows a conical-shaped tablet or caplet 200 which has swelled or enlarged end 202 and a relatively narrow end 204. Filler 206 is dispersed throughout tablet or caplet 200. FIG. 10 shows a generally-trapezoidal shaped tablet or caplet 208 which has a swelled or enlarged end 210 and a relatively narrow end 212. Similarly, filler 214 is dispersed throughout the tablet or caplet 208. As a result of the shape of tablets or caplets 200 and 208, swelled ends 202 and 210, respectively, are substantially heavier than the opposite narrow ends. Thus, the swelled or enlarged ends sink in the liquid with which the tablet or caplet is taken thereby effecting correct alignment of the tablet or caplet and movement of the tablet or caplet through the throat and into the esophagus.

3) Softgels

In accordance with the present invention, the weight of softgels is increased to improve swallowability thereof. In one embodiment of the present invention, increasing the weight of softgels is effected by the addition of a filler. Specifically, the filler is added to the ingredients, e.g. a solid sucrose portion. This is illustrated in FIG. 8. Softgel 100 comprises portions 102 and 104. Portion 102 is comprised only of ingredients. Portion 104 includes filler 106. In one embodiment, filler 106 is comprised of solid sucrose.

In another embodiment of the present invention, increasing the weight of softgels is accomplished by increasing the amount of a component. For example, if the component is a liquid excipient, then the amount of the excipient is increased. Increasing the amount of the component can also be realized by increasing the size or thickness of the softgel.

In another embodiment, the softgels can be configured that one side or portion of the softgel has concentrated weight and has indicia to indicate this end.

In a preferred embodiment, the percentage of total weight of the softgel that is due to the addition of the filler or increase in component is between about 15% and 90%, inclusive. More preferably, the percentage of total weight of the softgel that is due to the addition of the filler or increase in component is between about 25% and 75%, inclusive.

The increase in weight and/or density provides significantly improved swallowability of particularly light, small sized softgels (i.e. under 300 mg, 4/10 ml).

Gravity plays a significant role in the process of swallowing food. The role of gravity in swallowing food is described in *The Human Body, Volume on "Digestion"*, pp. 60–61, Torstar Books, 1984 and in *The ABC's of the Human Body*, Reader's Digest General Books, page 240, 1987. The relatively greater weight and/or density of the oral dosage forms of the present invention effect augmentation of the gravitational force that facilitates the downward passage of the oral dosage forms. Thus, the swallowability of the oral dosage forms is significantly increased.

Thus, the present invention provides new and improved oral dosage forms that:

a) solve the aforementioned problems discussed above that relate to the swallowability of oral dosage forms;

b) can be provided in the form of capsules, tablets, gelcaps and softgels;

c) interact with gravity to facilitate prompt and direct movement of the oral dosage form to the opening of and through the esophagus;

d) results in a relatively faster dissolution rate of the oral dosage form and relatively faster absorption rate of the medication provided by the oral dosage form;

e) can be produced with commercially available ingredients; and f) can be produced without exorbitant manufacturing costs.

The principals, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations in changes may be made by those skilled in the art without departing from the spirit of the invention. Accordingly, the foregoing detailed description should be considered exemplary in nature and not limited to the scope and spirit of the invention as set forth in the attached claims.

Thus, having described the invention, what is claimed is:

1. An oral dosage form for human ingestion configured to be swallowed in whole with a liquid, comprising:

a capsule having a first portion and a second portion attached to the first portion, each portion having an interior;

an active ingredient concentrated in the interior of the first portion; and a predetermined amount of filler concentrated in the interior of and adhered to the second portion of the capsule, the filler being chosen from the group consisting of sucrose, dextrose, lactose, fructose, microcrystaline cellulose, sorbitol, xylitol, isomalt, gelatin and starch, the filler having a predetermined weight that increases the density of the capsule to a predetermined density that effects sinking of the entire capsule in the liquid, the amount and concentration of the filler being such as to eliminate formation of regions within the interior of the second portion that are relatively low density with respect to the liquid with which the capsule is swallowed;

wherein the percentage of the total weight of the capsule that is due to the weight of the filler is between about 15% and 80%; and wherein the amount and concentration of the filler in the interior of the second portion significantly reduce the buoyancy of the capsule so as to cause the entire capsule to sink in the liquid.

2. The oral dosage form according to claim 1 further comprising an excipient in the interior of the first portion of the capsule with the active ingredient.

3. The oral dosage form according to claim 1 wherein the filler is a solid.

4. The oral dosage form according to claim 1 wherein the filler is a semi-solid.

5. The oral dosage form according to claim 1 wherein the capsule has indicia thereon to indicate the second portion of the capsule.

6. The oral dosage form according to claim 1 wherein said predetermined weight and concentration of the filler effect an increase in the density of the capsule to at least 1.0 g/ml.

* * * * *